United States Patent
Zeiler et al.

(10) Patent No.: US 8,992,529 B2
(45) Date of Patent: Mar. 31, 2015

(54) IMPLANT PLATE, METHOD AND FACILITY FOR THE MANUFACTURE THEREOF

(76) Inventors: Claudius Zeiler, München (DE); Ernst Wiedemann, München (DE)

( * ) Notice: Subject to any disclaimer, the term of this patent is extended or adjusted under 35 U.S.C. 154(b) by 667 days.

(21) Appl. No.: 10/635,919

(22) Filed: Aug. 6, 2003

(65) Prior Publication Data

US 2005/0021033 A1 Jan. 27, 2005
US 2012/0095464 A9 Apr. 19, 2012

Related U.S. Application Data

(63) Continuation of application No. PCT/DE02/00025, filed on Feb. 8, 2002.

(30) Foreign Application Priority Data

Feb. 16, 2001 (DE) ................................. 101 07 369

(51) Int. Cl.
*A61B 17/56* (2006.01)
*A61B 17/58* (2006.01)
*A61B 17/80* (2006.01)
*A61F 2/30* (2006.01)
*A61B 17/84* (2006.01)

(52) U.S. Cl.
CPC ......... *A61B 17/8061* (2013.01); *A61B 17/8085* (2013.01); *A61B 17/842* (2013.01)
USPC ........................................... 606/70; 606/280

(58) Field of Classification Search
USPC ............. 606/61, 69–71, 60, 65, 74, 280–299, 606/902–906, 915
See application file for complete search history.

(56) References Cited

U.S. PATENT DOCUMENTS 3,716,050 A * 2/1973 Johnston .......................... 606/69
3,842,825 A * 10/1974 Wagner ............................ 606/66

(Continued)

FOREIGN PATENT DOCUMENTS

DE 692 22 426 2/1998
DE 197 50 493 6/1999

(Continued)

OTHER PUBLICATIONS

Stratec and Mathys, presentation regarding PHILOS-Proximal Humerus Internal Locked System, Southamton meeting Apr. 2000, 30 pages.

*Primary Examiner* — Nicholas Woodall
*Assistant Examiner* — Christine Nelson
(74) *Attorney, Agent, or Firm* — Dickstein Shapiro LLP

(57) ABSTRACT

An implant plate according to the invention, for use in surgery or orthopedics, serves to stabilize a fracture of an upper-arm head or a fracture of a proximal upper arm. A head portion of the implant plate is fitted with at least one raised receiving member for a flexible fastening member on a side facing away from a bone. Each receiving member has an aperture extending substantially parallel to an outer edge or contour, and to an upper and lower side of the implant plate for threading, passing-through, and drawing together the flexible fastening member. The receiving member can be formed using process and plant technology from strip material, or using externally fabricated receiving members that are welded, press-welded, soldered, screwed, or riveted onto an outer side of the implant plate. The invention also comprises a method for manufacturing the implant plates.

11 Claims, 14 Drawing Sheets

(56) References Cited

U.S. PATENT DOCUMENTS

| | | | | |
|---|---|---|---|---|
| 4,011,863 A * | 3/1977 | Zickel | | 606/299 |
| 4,157,715 A * | 6/1979 | Westerhoff | | 606/60 |
| 4,263,904 A * | 4/1981 | Judet | | 606/74 |
| 4,364,382 A * | 12/1982 | Mennen | | 606/283 |
| 4,454,876 A * | 6/1984 | Mears | | 606/69 |
| 4,513,744 A * | 4/1985 | Klaue | | 606/282 |
| 4,565,193 A * | 1/1986 | Streli | | 606/69 |
| 4,573,458 A * | 3/1986 | Lower | | 606/69 |
| 4,628,923 A * | 12/1986 | Medoff | | 606/65 |
| 4,800,874 A * | 1/1989 | David et al. | | 606/69 |
| 4,988,350 A * | 1/1991 | Herzberg | | 606/65 |
| 5,006,120 A * | 4/1991 | Carter | | 606/71 |
| 5,015,248 A * | 5/1991 | Burstein et al. | | 606/74 |
| 5,190,545 A * | 3/1993 | Corsi et al. | | 606/74 |
| 5,197,966 A * | 3/1993 | Sommerkamp | | 606/69 |
| 5,409,489 A * | 4/1995 | Sioufi | | 606/80 |
| 5,578,036 A * | 11/1996 | Stone et al. | | 606/281 |
| 5,586,985 A * | 12/1996 | Putnam et al. | | 606/86 B |
| 5,591,168 A * | 1/1997 | Judet et al. | | 606/65 |
| 5,607,430 A * | 3/1997 | Bailey | | 606/74 |
| 5,611,354 A * | 3/1997 | Alleyne | | 128/846 |
| 5,674,222 A * | 10/1997 | Berger et al. | | 606/69 |
| 5,718,704 A * | 2/1998 | Medoff | | 606/69 |
| 5,728,099 A * | 3/1998 | Tellman et al. | | 606/65 |
| 5,797,916 A | 8/1998 | McDowell | | |
| 5,810,824 A | 9/1998 | Chan | | |
| 5,853,413 A * | 12/1998 | Carter et al. | | 606/69 |
| 5,938,664 A * | 8/1999 | Winquist et al. | | 606/69 |
| 6,007,536 A * | 12/1999 | Yue | | 606/60 |
| 6,096,040 A | 8/2000 | Esser | | |
| 6,221,073 B1 * | 4/2001 | Weiss et al. | | 606/60 |
| 6,338,734 B1 * | 1/2002 | Burke et al. | | 606/69 |
| 6,358,250 B1 * | 3/2002 | Orbay | | 606/86 B |
| 6,440,131 B1 * | 8/2002 | Haidukewych | | 606/60 |
| 6,488,685 B1 * | 12/2002 | Manderson | | 606/69 |
| 6,730,090 B2 * | 5/2004 | Orbay et al. | | 606/69 |
| 7,207,993 B1 * | 4/2007 | Baldwin et al. | | 606/70 |
| 2004/0116931 A1 * | 6/2004 | Carlson | | 606/70 |

FOREIGN PATENT DOCUMENTS

| | | |
|---|---|---|
| DE | 697 23 883 | 9/2004 |
| EP | 0791338 A2 | 8/1997 |
| EP | 0934731 A1 | 8/1999 |
| WO | WO-98/09578 | 3/1998 |

* cited by examiner

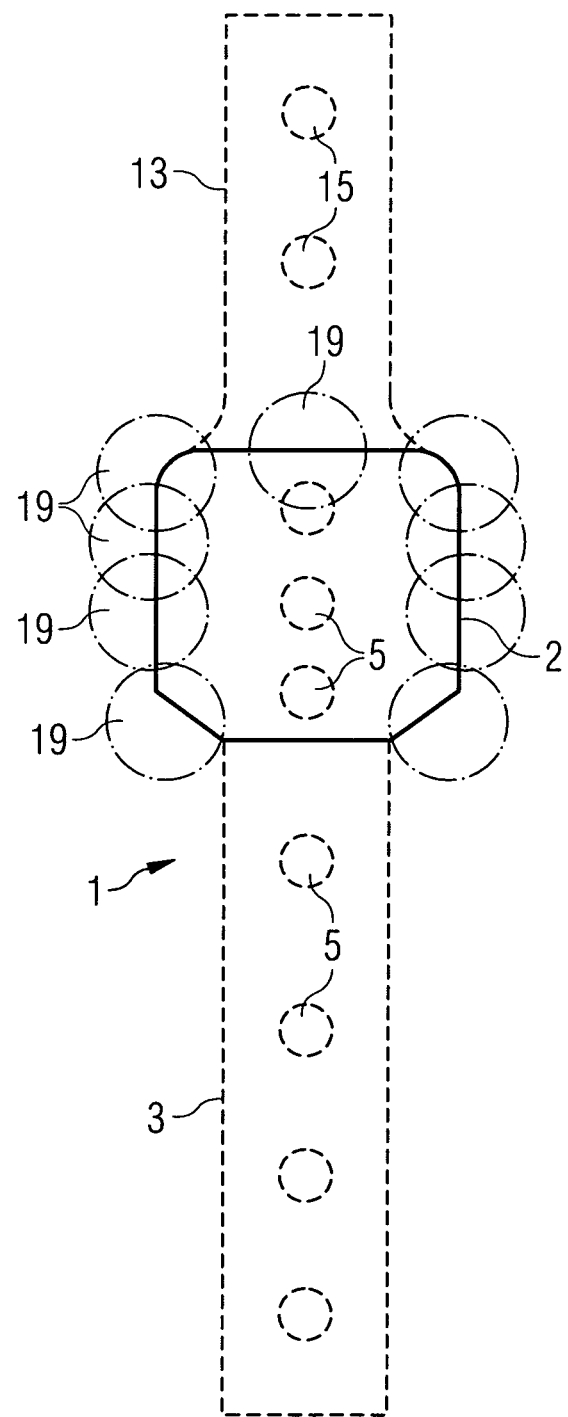

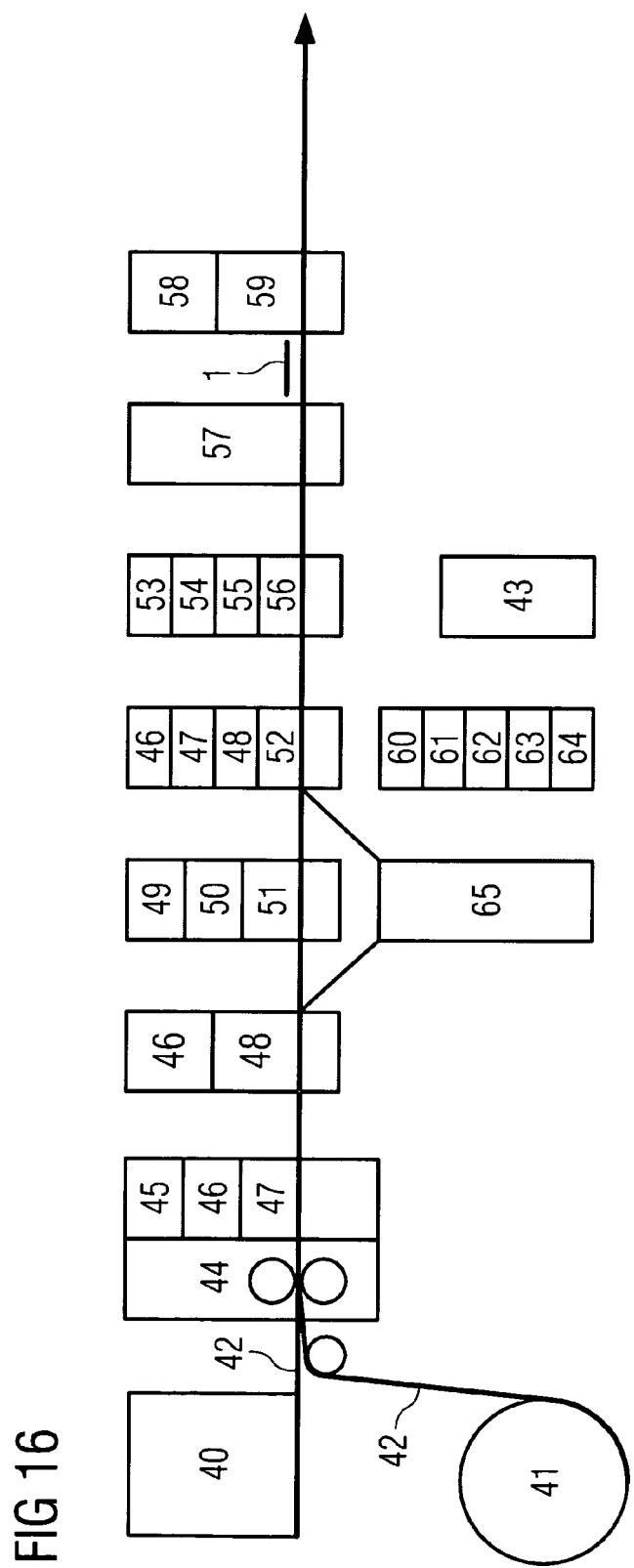

ated perpendicularly to the longitudinal axis of the rod-shaped implant. At the free upper end and between the two upper-arm head screws of the implant region, drill boles are provided to extend parallel to the upper and the lower side of the rod-shaped implant, serving to accommodate purse-string wire-sutures, and resorbable or non-resorbable sutures for resetting torn-out tubercules.

The specific shoe-horn shaped implant plate for stabilizing a fracture of an upper-arm head, as known from the Prospectus "PHILOS-Proximal Humerus Internal Locked System" November 00/EMA/Docseries VI, of the firms of Stratec/Mathys, has in the head-end portion, drill holes close to the edge for accommodating wire cerclages or resorbable or non-resorbable suture material, but nevertheless, this construction makes it difficult to thread these fastening members, and to loop them around the plate edge, so that because of the short guiding length, this suture material may become damaged, and the wire cerclages may be jammed. In both cases, the fastening member may be ruptured. Furthermore, the fastening members first prevent a large plate area from bearing against the bone surface, and then render difficult a subsequent threading operation. The square-bar shaped implant known from DE 197 50 493 A1 has two drill holes distributed on its massive, head-end portion, that extend parallel to the upper and lower end of the implant, however, this embodiment cannot be simply converted to an implant plate. The two drill holes are made possible only because the massive, head-near portion of the implant is of a material that has been adequately reinforced in comparison with that of the shaft-near portion. Furthermore, this implant is not easily usable in surgical practice, because the massive proximal upper-arm head-screws cause an additional loss of bone owing to a necessary preliminary boring operation. Furthermore, a massive embodiment of this kind is, not necessary, because of the relatively small load acting on this upper extremity, and interferes with surrounding parts of soft body tissue.

IMPLANT PLATE, METHOD AND FACILITY FOR THE MANUFACTURE THEREOF

This is a continuation of International Patent Application No. PCT/DE2002/000025, filed Feb. 8, 2002, which claims priority to German Patent Application No. 10107369.0, filed Feb. 16, 2001.

BACKGROUND OF THE INVENTION

1. Field of the Invention

The invention relates to an implant plate, and a method for semi-automatic or fully automatic manufacture of implant plates for use thereof in surgery and/or orthopedics.

The invention therefore relates to an at least one-part, internal humerus plate. In addition, the invention comprises a method for semi-automatic or fully automatic manufacture of implant plates for use as a product directly manufactured by process technology and plant engineering, in surgery and/or orthopedics. With the implant plate according to the invention, a substantially improved stabilization of a fracture of a head of an upper arm, and/or a fracture of a proximal upper arm is attained.

2. Description of the Related Art

General prior art includes metallic implant plates having a substantially constant thickness or strength along a longitudinal and lateral cross-section. With these plates, bone fractures are fixed in position and held together with bone screws during processes of healing. From the Prospectus "PHILOS-Proximal Humerus Internal Locked System", November 00/EMA/Docseries VI, of the firms of Stratec/Mathys, a specific shoe-horn shaped implant plate for stabilizing a proximal humerus fracture is known. Drill holes are provided along the middle plate section for bone screws which are directed, on the one hand, into the upper-arm head with the spongy tubercle and, on the other hand, into the proximal shaft region of the humerus. These shoe-horn shaped implant plates are formed to be wider in the region near the head of the upper arm, and narrower in the shaft region of the humerus. The region near the head of the implant plate has at least four drill holes, and the shaft region at least three drill holes. Furthermore, the region near the head of the implant plate has at least six drill holes close to the edge for accommodating metallic wire material, or resorbable and non-resorbable thread material, for holding together the fracture parts of the head. From DE 197 50 493 A1 an implant is known for use in surgery for stabilizing a humerus-head fracture by means of a screw. Although in DE 197 50 493 A1 this implant is repeatedly also described as being a plate, the constructional configuration is substantially based on that of a massive square bar, the shaft region of which has a reduced material thickness, and the head-near region of which has, by comparison, a substantially doubled material thickness. The head-near region of the square bar is shaped to be substantially concave towards the humerus head. The fabrication of the basic spatial shape of the implant requires costly measures of processing by forging, pressing, and/or cutting operations. In the head-near region, this implant has two guides for bone screws, with which these screws are stably held at an angle to the plate for setting the fracture. Preferably, the screws are releasably fixed by means of a clamping device to prevent a rotation of the screw shaft, and a displacement along the direction of the screw shaft. Suitable for this is a special screw having a thread outer diameter that is greater than the diameter of the adjoining shaft. In order to ensure reliable guiding, the shaft diameter is enlarged in the region of the screw head. In addition, the implant has drill holes for shaft screws, which are substan-

BRIEF SUMMARY OF THE INVENTION

The invention is based on the problem of creating an implant plate giving a substantially improved stabilization of a fracture of an upper arm and/or a fracture of a proximal upper arm. Apart from this, a method for semi-automatic or fully automatic manufacture of the implant plates According to the invention, this object is achieved by an implant plate for stabilizing a fracture of an upper-arm head or a fracture of a proximal upper arm, and formed to a flat longitudinal channel for bearing against a bone, comprising: a head-end portion and a shaft-end portion, forming a spoon-shaped outer contour; holes for bone screws; and at least one raised receiving member for a flexible fastening member, such as a wire cerclage or a surgical suture material, disposed at an outer edge or contour of a side of the head-end portion of the implant plate facing away from the bone; wherein the at least one receiving member has an aperture extending substantially parallel to an outer edge or contour, and to the upper and lower side of the head-end portion of the implant plate, for threading, passing-through, and drawing together the flexible fastening member; and the at least one receiving member is provided with the aperture by being formed to be one of a tube, an eyelet, a round hook, and a ridge perpendicular to an outer edge of the head-end portion and having a drill hole, or a hole produced by a laser device or by punching.

Furthermore, the above object is achieved by a method for manufacturing an implant plate for stabilizing a fracture of an upper-arm head or a fracture of a proximal upper arm, and formed to a flat longitudinal channel for bearing against a bone, the implant plate having a head-end portion and a shaft-end portion, a spoon-shaped contour, and holes for bone screws; comprising the step of: fitting the head-end portion of the implant plate with at least one raised receiving member for a flexible fastening member, such as a wire cerclage or a surgical suture material, disposed at an outer edge or contour of a side of the head-end portion that faces away from the bone; and comprising the further step of: providing the at least one receiving member with an aperture extending substantially parallel to an outer edge or contour, and to the upper and lower side of the head-end portion facing away from the bone, for threading, passing through, and drawing together the flexible fastening member, by forming the receiving member to be one of a tube, an eyelet, a round hook, and a ridge perpendicular to an outer edge of the head-end portion and having a drill hole or a hole produced by a laser device or by punching.

SUMMARY OF THE INVENTION

The principle of the solution on which the invention is based consists substantially of a spoon-shaped implant plate having drill holes and/or oblong holes for bone screws being provided for stabilizing a fracture of an upper-arm head or an upper arm, the plate having at least one raised receiving member for flexible fastening members, and the receiving member being provided on the side facing away from the bone and on the longitudinal axis at the upper edge of the spoon-shaped portion. According to one embodiment, at least one receiving member can be disposed at each longitudinal edge on the side of the implant plate facing the bone. Each receiving member has an aperture extending substantially parallel to the respective plate edge. The apertures are preferably designed to be eyelets, round hooks, or tubes, wherein slightly curved and relatively long guide paths substantially facilitate and improve an operation of threading, passing through, and drawing together the employed flexible fastening members which are wound around the fracture. The entry and exit edges of the apertures must be blunted, rounded and/or smoothed, in order that the flexible fastening members may not be damaged or destroyed. Each implant plate may have a blade disposed along the longitudinal axis, starting out from the upper edge of the spoon-shaped portion of the implant plate, the blade being driven into the humerus head in an angled state. The blade has at least one drill hole having at least one screw-thread into which an upper-arm head-screw is screwed to extend obliquely upwards from the head-end portion or head portion of the implant plate. In order to allow at least one upper-arm head-screw to be passed through the head- and shaft-end portions, the implant plate has at least one respective drill hole and/or oblong hole. The insertion of the upper-arm head-screws from the implant plate to the angled blade creates a stable angled connection, whereby the support of the blade on the humerus head and the implant plate at the upper-arm head and the proximal upper arm is improved. The receiving members disposed close to the edge on the side of the implant plate facing away from the bone, decisively improve the operations of threading, guiding and drawing together the flexible fastening member with which the fracture of the upper-arm head and/or the proximal upper arm is additionally stabilized. This constructive design of the implant plate thus ensures the operations of inserting, threading, and passing-through, and also of tightening the flexible fastening members even after the plate has been secured to the bone.

The principle of the solution in accordance with the invention also comprises a method according to which the implant plates are fabricated semi- or fully automatically, and also semi- or fully continuously, by programmed control from metallic flat-strip or strip material, consisting for example of implant steel, titanium or titanium alloys and the like. According to one embodiment, the flat strip which is kept available having the necessary measurements, either cut to length from a stacking magazine, or in the form of a coil, may be first cold-worked in order to produce, for example, naps, discontinuous grooves, and the like on the surface of the side of the implant plate intended to bear against the bone, in order that sustenance of the periosteum and the bone be maintained during subsequent use of the inserted implant plate. The flat strip may also be kept available, suitably provided with a surface profile by means of preceding hot or cold rolling, as a starting material for the method of the invention. Thereupon the flat strip is worked by machining or the like according to a previously determined configuration in order to produce apertures such as drill-holes, openings, and the like, having a relatively large diameter for the bone screws, and apertures such as drill holes, openings, and the like, having a relatively small diameter, in the receiving members that are to be formed from the flat strip material, for flexible fastening members. At the same time, or subsequently, forming-cuts such as parallel slits, oblique cuts, partial cuts and the like are made close to the edge of the flat strip, as needed for forming the receiving members, and possibly also the blade, for example by cutting, punching, laser treatment, machining, eroding and the like. Also simultaneously, or subsequently, having regard to the later use of the implant plate, the regions of the flat strip prepared for forming the receiving members close to the edge are cold-formed, i.e. deep drawn, bent, rolled, angled and the like, in the direction of the side facing away from the bone, so that the receiving members for the flexible fastening members on the side of the implant plate facing away from the bone are visibly raised, but only to a small height. The apertures such as drill holes, openings, and the like, previously formed in the receiving members, are then positioned close to the edge to be substantially parallel to the course of the plate edge, and also to the upper and lower side of the implant plate yet to be completed. Cold-forming may also be applied to forming spaced regions of weakened material extending across the longitudinal axis, for later use as strap hinges or positions of separation for producing interlocking hinges, and for sharpening the edges at the free end of the blade. Subsequently the flat strip, as prepared to this extent, may be cold-formed to a flat longitudinal channel substantially not including the blade region, in order to optimize a bearing of the implant plate, in later use, against the bone. Subsequently the implant blanks having the spoon-shaped outer contour are produced from the bowed strip material by material removal, for example by punching, laser treatment, cutting, machining, and the like, and singled at the same time.

According to an embodiment of process technology, a flat strip of a width greater than the width of the spoon-shaped portion of the implant plate is used in order to punch, cut by laser, cut, and the like, wide or narrow rectangular ridges from the excess plate-edge region. By edge-rolling these ridges in the direction of the upper side of the implant plate facing away from the bone, tubular or round-hook shaped receiving members of low height are formed for drawing-through flexible fastening members. A singling operation on the flat strip that has been prepared to this extent, to yield implant blanks, is also effected by suitable removal of material. The singled implant plate blanks are subsequently imparted with the predetermined flat channel profile by cold-working.

According to a preferred embodiment of process technology, instead of the preparatory measures of process technology for forming the receiving members from the flat strip material, externally prefabricated receiving members for the flexible fastening members, having the shape of tubular sections, round hooks, eyelets and the like of a low projecting height and an opening cross-section matched to the diameters of the flexible fastening members, may be attached to the surface of the singled implant blanks close to the edges before or after the bowing, i.e. flat-channel shaping of the blanks by cold-forming, welding, press-welding, soldering, screwing, and the like.

The implant plate blanks fitted with receiving members for flexible fastening members attain the final state of fabrication following deburring, rounding of edges, and cleaning. According to an embodiment of process technology, the implant plates may be surface-finished by galvanic, electrochemical, or vacuum-technological methods such as the CVD method (Chemical Vapor Deposition). The implant plates are sterilized and supplied for surgical use suitably packed.

A facility associated with the invention is of linear and modular construction, and comprises substantially program-controlled, semi or fully automatically operating and timed fabrication machines or automatic machines with which the flat strip is processed to form the receiving members for flexible fastening members, and with which the implant plate, possibly including the blade, is also made.

According to an embodiment of plant technology, the individual devices may be disposed for operative cooperation in a linear array, or opposite to each other, or in a meandering configuration, or also in a roundabout, turnstile, or double star arrangement.

In accordance with the invention, the implant plates, and also the implant plates directly produced by the method, possibly using the plant, are utilized for stabilizing fractures of an upper arm head and a proximal arm.

The invention will be described in greater detail in the drawings.

BRIEF DESCRIPTION OF THE DRAWINGS

FIG. 5 shows a front view of an implant plate based on FIGS. 1A and 3A, with modifiable locating positions, shown as circles, for receiving members in a region close to the edge of the head-end portion, for additional stabilization of a fracture of an upper-arm head and a proximal upper arm.

FIG. 16 shows a process operation and a linear modular configuration of a facility for manufacturing the implant plates according to the invention.

Figure 1A:
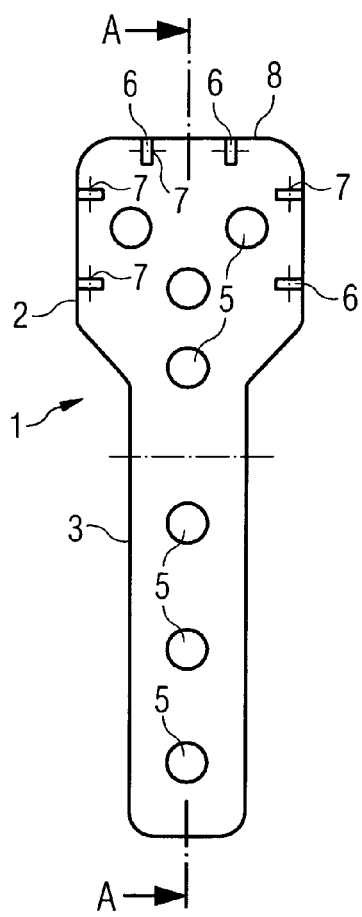
FIG. 1A shows a front view, with a drawn-in longitudinal sectional line A-A, of a spoon-shaped implant plate for additional stabilization of a fracture of an upper-arm head, and/or of a proximal upper arm, the implant plate having drilled holes and/or oblong holes for bone screws in a spoon- and shaft-end portion, and also ridge-shaped receiving members for flexible fastening members in a region close to the edge of the head-end portion or spoon portion of the implant plate.

Any reference numerals which have not been inserted become evident from preceding or subsequent Figures and the descriptions pertaining thereto.

DETAILED DESCRIPTION OF PREFERRED EMBODIMENTS

The invention comprises the design of the structure of an implant plate for stabilizing a fracture of an upper-arm head and/or a fracture of a proximal upper arm, the implant plate having, in addition to drill holes for upper-arm head-screws and shaft screws, receiving members disposed close to the edge on the side of the head portion facing away from the bone, for flexible fastening members such as wire cerclages or surgical suture material. The implant plate has a substantially uniform thickness of material of about 0.5 to 6.5 mm, preferably of 0.8 to 3.5 mm. The head-end portion of the implant plate is formed to be spoon-shaped. In comparison with the head-end portion, the shaft-end portion of the implant plate is formed to be narrower, having a flat stem-shape. Furthermore, the spoon-shaped implant plate is of slightly convex curvature, and a cross-section that is slightly bowed, or of hollow-ground shape, or formed as a shallow channel-profile. The head-end portion has at least one drill hole and/or oblong hole for upper-arm head-screws. The shaft-end portion has at least one drill hole and/or oblong hole for shaft screws. In an embodiment, at least three receiving members, formed as ridges, for fastening members are provided close to the edge on the spoon-shaped portion of the implant plate to protrude from the side facing away from the bone. These eyelet-shaped receiving members facilitate rapid threading of the flexible fastening member, such as a wire cerclage or surgical suture material.

Figure 1B:
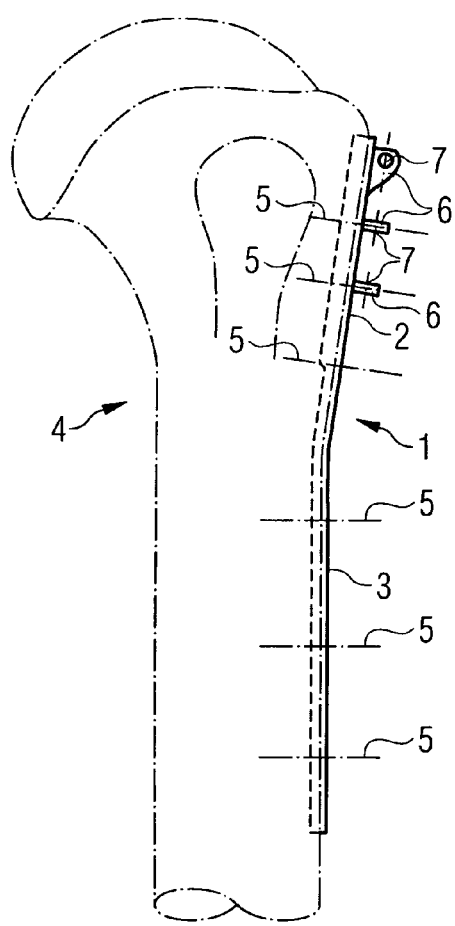
FIG. 1B shows a side view of the arrangement of FIG. 1A of an implant plate on an upper-arm head and on a proximal upper arm along a longitudinal section A-A.

FIGS. 1A and 1B show an implant plate 1 according to the invention, having a head-end portion 2 and a shaft-end portion 3. The head-end portion 2 has two drill holes 5, equally spaced from the longitudinal axis A-A of the implant plate, and two further drill holes 5, located on the longitudinal axis A-A, for upper-arm screws. The shaft-end portion 3 has three drill holes 5, equally spaced along the longitudinal axis A-A, for shaft screws. The head-end portion 2 has, on the surface of the implant plate 1 facing away from the bone 4, six substantially uniformly distributed, ridge-shaped receiving members 6 having apertures 7 that are designed as drill holes 14 for not shown flexible fastening members. The apertures 7 must extend substantially parallel to the upper and lower side of the implant plate 1, and also parallel to the outer edge or contour 8 of the head portion 2, whereby threading and guiding of the flexible fastening members, and also looping of the flexible fastening members around, and drawing together the fracture is decisively improved. In the illustrated embodiment, the implant plate 1 is designed to be of one piece, and of slight convex curvature, in order to bear well against the upper-arm head and the proximal upper arm.

Figure 2A:
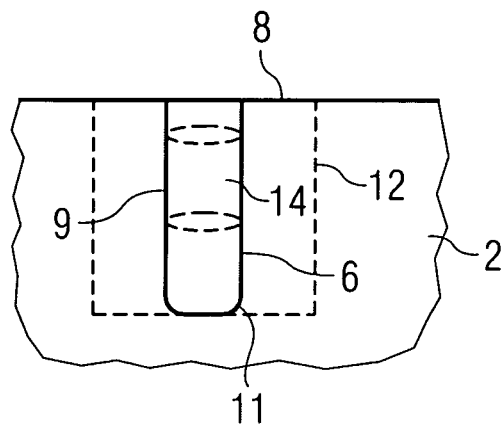
FIGS. 2A-2C show a magnified front and side view, and also a plan view, of the ridge-shaped receiving member of FIGS. 1A-1C, with a sectional line B-B through the side view.
Figure 2B:
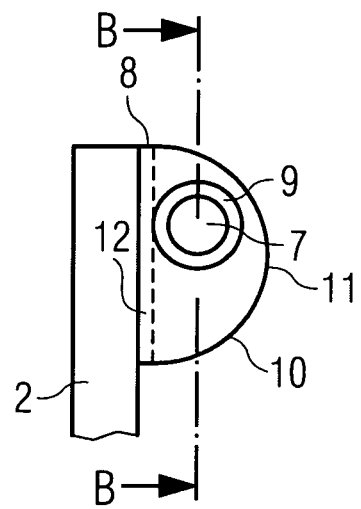
Figure 2C:
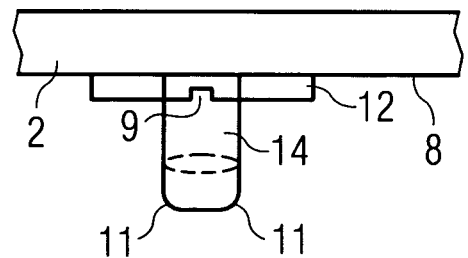

FIGS. 2A-2C show a magnified front and side view, and also a plan view, of the receiving member 6 of FIGS. 1A and 1B, formed as a ridge 10. Each ridge 10 is aligned to substantially perpendicular to an outer edge 6 of the head-end portion 2 of the implant plate 1, and has a drill hole 14 representing the aperture 7. Outer edges 9 of the drill hole 14 are rounded, so that the not shown flexible fastening member may be easily threaded and guided without being damaged. The edges 11 of the ridge 10 have also been blunted or rounded, to protect tissue. In accordance with the side view, the ridge 10 is formed to be of semi-circular shape. The ridge 10 may be of semi-oval shape, square, or rectangular, the corners and edges 11 being blunted or rounded in each case, in order to protect tissue. The ridge 10 may be disposed on a plate-shaped, round, square, rectangular, triangular, or oval base 12. The base 12 may be welded, pressure welded, soldered, or screwed onto the side of the implant plate 1 facing away from the bone 4, at a position close to the edge. The base 12 may also be dispensed with, so that the ridge 10 may be suitably fixed directly onto the implant plate 1, at a predetermined location close to the edge.

Figure 3A:
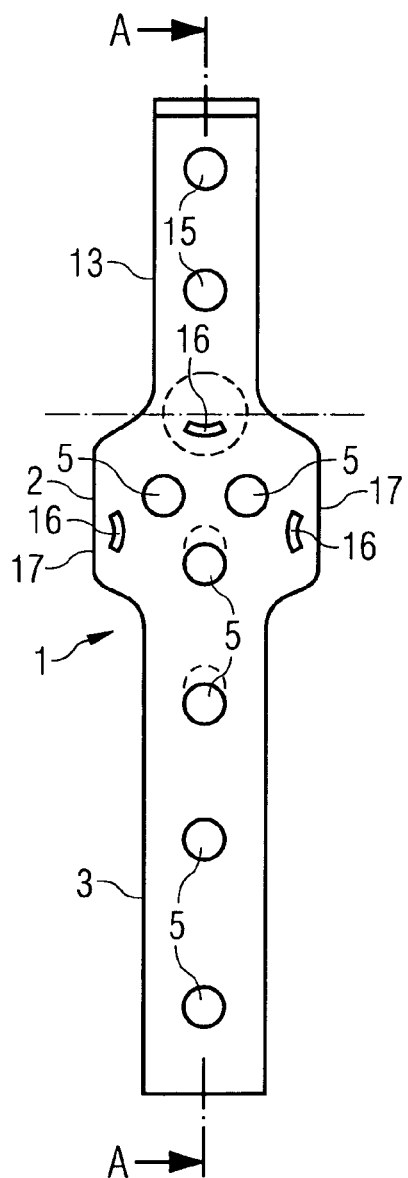
FIG. 3A shows a front view of a spoon-shaped implant plate with a widened head-end portion or spoon portion, and a narrower shaft-end portion or shaft portion, having distributed drill holes and/or oblong holes for bone screws and tubular-shaped receiving members for flexible fastening members in a region close to the edge of the head-end portion, and also a blade extending from the upper end of the head-end portion for additional stabilization of a fracture of an upper-arm head and a proximal upper arm.
Figure 3B:
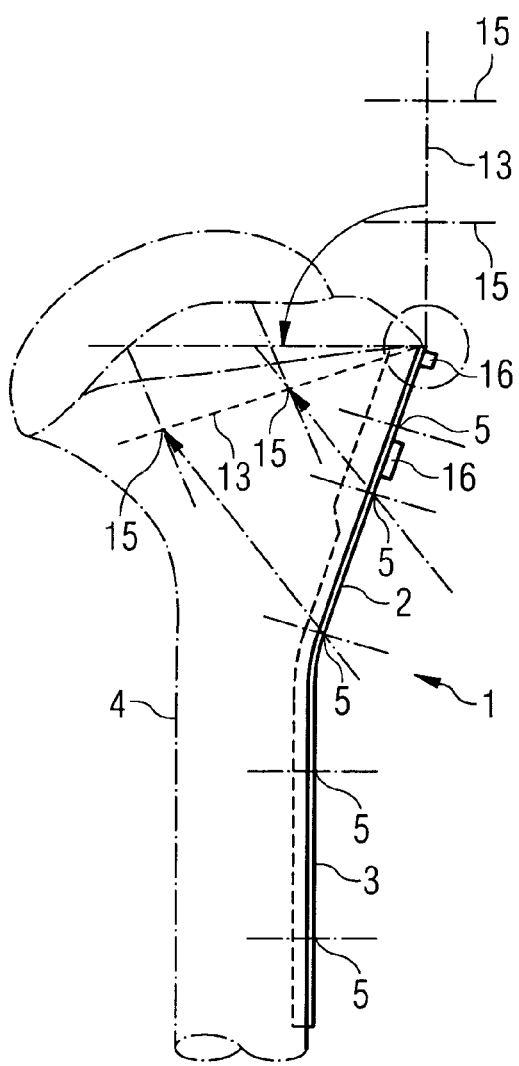
FIG. 3B shows a side view of the arrangement of FIG. 3A of the spoon-shaped implant plate on an upper-arm head and a proximal upper arm, with a driven-in blade, and also the tubular receiving members.

FIGS. 3A and 3B illustrate a spoon-shaped implant plate 1 having a blade 13 that extends from the head-end portion 2, and is disposed along an extension of the longitudinal axis A-A of the implant plate, and has a sharp edge at the end. Within the portion of the blade 13 lying along this longitudinal axis of the implant plate 1, two spaced drill holes 15 having at least one cut-in thread are provided. The blade 13 can be suitably bent at an angle depending on the fracture of the upper-arm head, and driven into the upper-arm head. The head-end portion 2 of the implant plate 1 has two drill holes 5 equally spaced from the longitudinal axis A-A, and two drill holes 5 lying on the longitudinal axis A-A, for upper-arm head-screws. The shaft-end portion 3 has three drill holes 5 equally spaced from each other along the longitudinal axis, for shaft screws. The two drill holes 5 that are spaced from each other on the longitudinal axis A-A may also be designed to be oblong holes for the upper-arm head-screws. According to the illustrated embodiment, two upper-arm head-screws, in particular the two upper-arm head-screws lying on the longitudinal axis A-A, may be directed towards the two drill holes 15 of the blade 13 and screwed into the at least one thread of the drill holes 15. This embodiment makes possible a locking of the implant plate to prevent it from moving out of the humerus head, so that a stable angular connection between the bone 4 or humerus head, the blade 13, and the implant plate 1 is created. The combination of this with the flexible fastening members 29 passing through the receiving members 16, and the three tubular receiving members 16 disposed close to the edge, results in the achievement of an extremely effective fracture stabilization within a substantially shortened operating time.

Figure 4A:
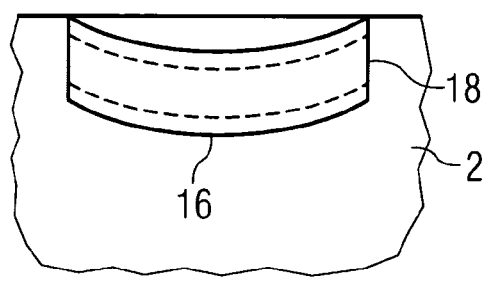
FIGS. 4A-4C show a front and side view, and also a plan view of a tubular receiving member of FIGS. 3A and 3B in a region close to the edge of the head-end portion.
Figure 4B:
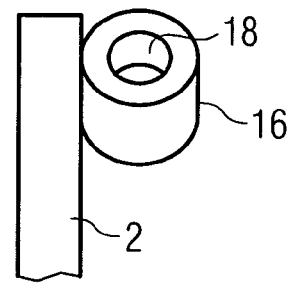
Figure 4C:
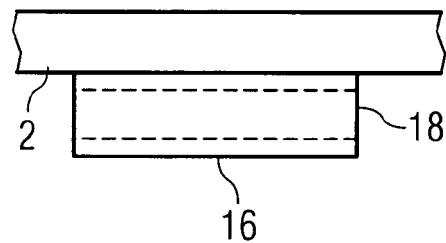

FIGS. 4A-4C illustrate a magnified front and side view, and also a plan view, of a tubular-shaped receiving member 16 of FIGS. 3A and 3B. A tubular-shaped receiving member 16 is disposed on the blade-side edge region of the head-end portion 2 of the implant plate 1 across the longitudinal axis A-A and parallel to the upper side of the implant plate 1. Furthermore, a tubular-shaped receiving member 16 is disposed at each of the opposite longitudinal edges 17 of the head-end portion 2 to be close to the edge and also substantially parallel to the longitudinal edge 17 and parallel to the upper side of the implant plate 1. The edges of the exits 18 of the tubular receiving members 16 are rounded. The exits 18 of the tubular receiving members 16 are directed towards the associated outer edge or contour 8 of the implant plate 1.

FIG. 5 illustrates the head-end portion 2 of the implant plate 1 with the blade 13, and the shaft-end portion 3, both being shown only with broken lines. In the region of the outer edge or contour 8 of the head-end portion 2, variable locating positions 19, indicated by means of circular broken lines, for further embodiments of receiving members 6 for flexible fastening members are provided.

Figure 6A:
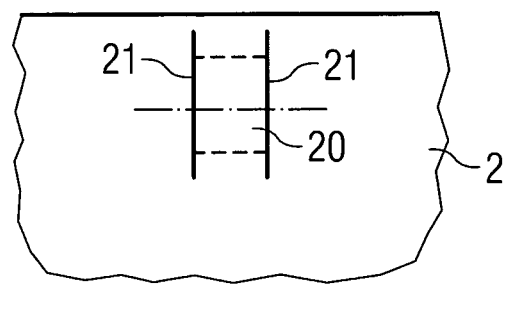
FIGS. 6A-6C show a front and side view, and also a plan view of an eyelet-shaped receiving member, formed from a deep-drawn slit close to an edge, for a flexible fastening member, in a modification of the arrangement of FIG. 5.
Figure 6B:
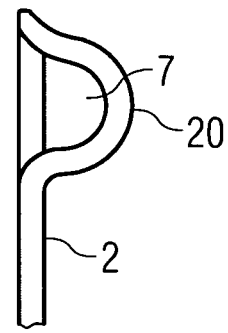
Figure 6C:
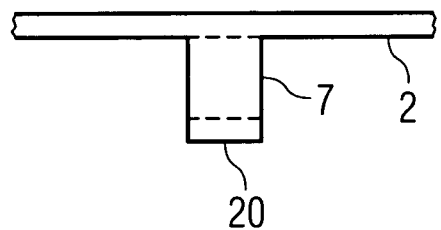

FIGS. 6A-6C illustrate a front- and side view, and also a plan view, of a receiving member 20 having an eyelet-shaped aperture 7 for flexible fastening members, as usable with the locating possibilities 19 of FIG. 5. This receiving member, having an eyelet-shaped aperture 7, has been produced by deep drawing from a parallel slit 21 close to the edge of the implant plate 1. All edges intended to contact the flexible fastening member and the tissue have been rounded.

Figure 7A:
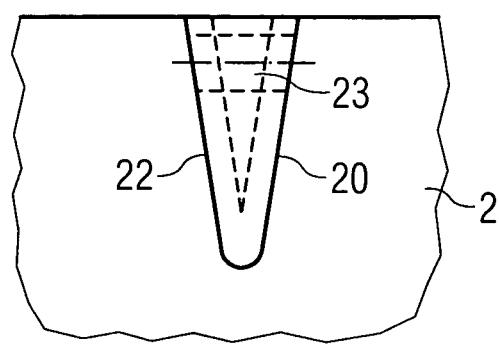
FIGS. 7A-7C show a front and side view, and also a plan view of an eyelet-shaped receiving member, formed from a fold close to an edge, for a flexible fastening member, in a modification of the arrangement according to FIG. 5.
Figure 7B:
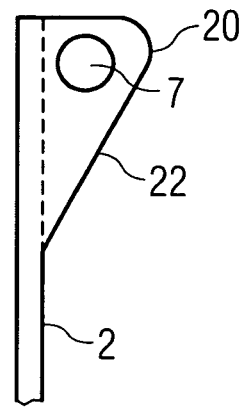
Figure 7C:
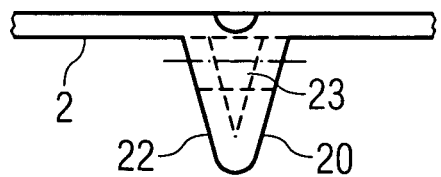

FIGS. 7A-7C illustrate a front and side view, and also a plan view, of a further receiving member 20 having an eyelet-shaped aperture 7 for flexible fastening members, as usable with the locating possibilities 19 of FIG. 5. This eyelet-shaped aperture 7 of the receiving member 20 has been produced by deep drawing a region close to the edge of the implant plate 1 to a fold 22, and by providing a through drill hole 23. All edges intended to contact the flexible fastening member and the tissue have been rounded.

Figure 8A:
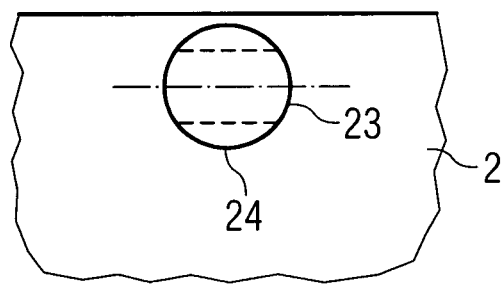
FIGS. 8A-8C show a front and side view, and also a plan view of an eyelet-shaped receiving member, formed from a deep-drawn cup close to an edge, for a flexible fastening member, in a modification of the arrangement according to FIG. 5.
Figure 8B:
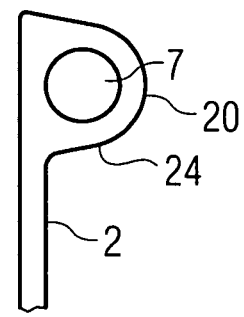
Figure 8C:
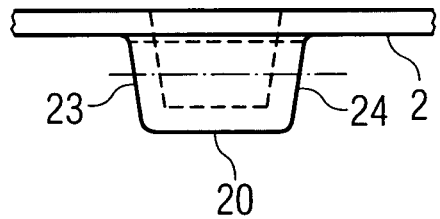

FIGS. 8A-8C illustrate a front and side view, and also a plan view, of a further receiving member 20 having an eyelet-shaped aperture 7 for flexible fastening members, as usable with the locating possibilities 19 of FIG. 5. This receiving member 20 with the eyelet-shaped aperture 7 has been produced by deep drawing a region close to the edge of the implant plate 1 to a cup 24, and by providing a through drill hole 23.

Figure 9A:
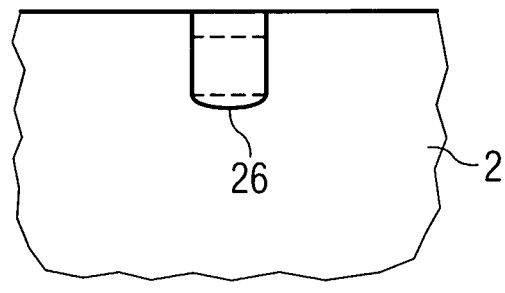
FIGS. 9A-9C show a front and side view, and also a plan view of a receiving member, cut from excess plate material close to an edge in the form of a tab and bent to hook-shape, for a flexible fastening member, in a modification of the arrangement according to FIG. 5.
Figure 9B:
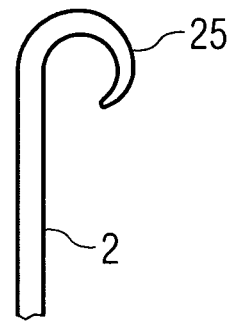
Figure 9C:
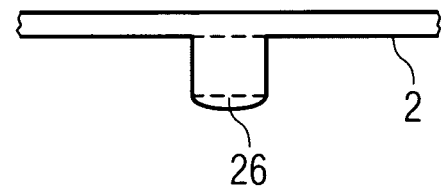

FIGS. 9A-9C illustrate a front and side view, and also a plan view, of a round-hook shaped receiving member 25 for flexible fastening members 29, as usable with the locating possibilities 19 of FIG. 5. This round-hook shaped receiving member 25 has been produced by punching a narrow strip-shaped extension 26 from an excess edge region of the implant plate 1, and subsequently edge-rolling the free end of the extension 26 to a round hook 25. All edges intended to contact the flexible fastening member and the tissue have been rounded.

Figure 10A:
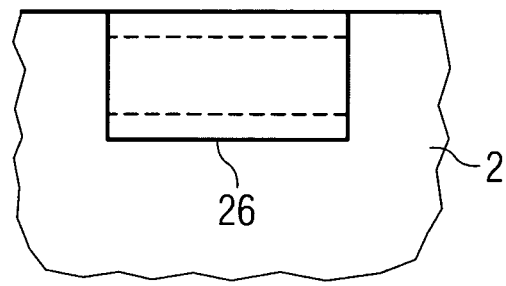
FIGS. 10A-10C show a front and a side view, and also a plan view of a receiving member, cut from excess plate material close to an edge in the form of a flange and bent, for a flexible fastening member, in a modification of the arrangement according to FIG. 5.
Figure 10B:
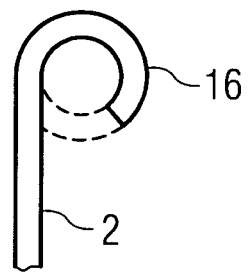
Figure 10C:
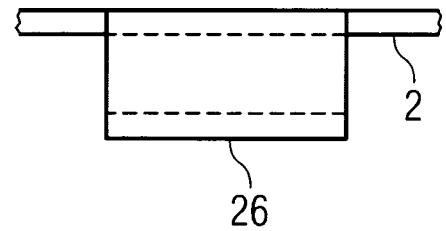

FIGS. 10A-10C illustrate a front and side view, and also a plan view, of another tubular receiving member 16 for flexible fastening members, as usable with the locating possibilities 19 of FIG. 5. This tubular receiving member 16 has been produced by punching a wide rectangular extension 26 from an excess edge region of the implant plate 1, and subsequently edge-rolling the free end of the extension 26 to a tubular receiving member 16. All edges intended to contact the flexible fastening member and the tissue have been rounded.

Figure 11A:
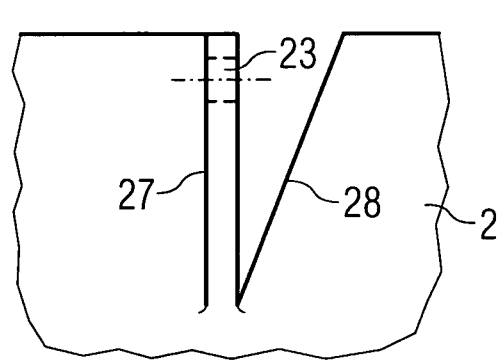
FIGS. 11A-11C show a front and a side view, and also a plan view of a triangular receiving member, cut obliquely from plate material close to an edge and bent at an angle, for a flexible fastening member, in a modification of the arrangement according to FIG. 5.
Figure 11B:
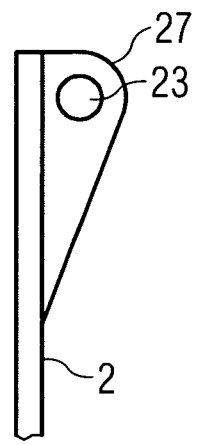
Figure 11C:
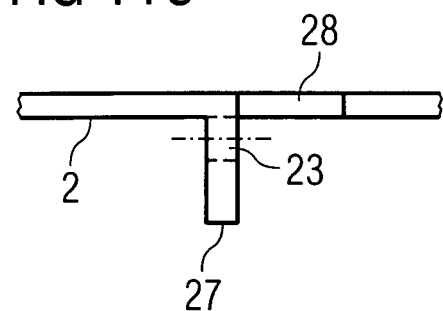

FIGS. 11A-11C illustrate a front and side view, and also a plan view, of a triangle-shaped receiving member 27 provided with a drill hole 23 and formed by means of an oblique cut 28 close to the edge in the strip material, and subsequently bending-away material substantially vertically from the upper side of the implant plate 1. All edges intended to contact the flexible fastening member and the tissue have been rounded.

Figure 12:
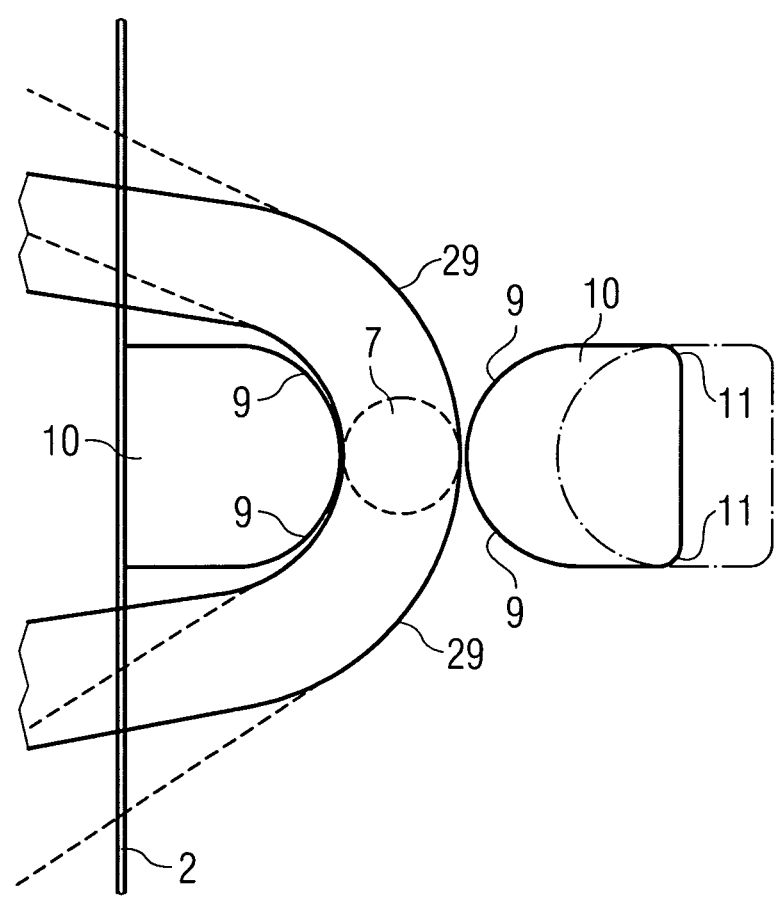
FIG. 12 shows the ridge-shaped receiving member for a flexible fastening member in a magnified view of the section B-B of the side view of FIG. 2B.

FIG. 12 shows a magnified view of the ridge 10 along the sectional line B-B of the side view of FIG. 2B. According to this, the aperture 7, i.e., the drill hole 14, is occupied by a flexible fastening member 29. The drill hole 14 may be conformed to the diameter of the flexible fastening member 29, but may also be larger in order to facilitate threading, and possibly multiple threading-through of the flexible fastening member 29.

All edges 8, 9 of the implant plate 1 based on embodiments of the invention, which may contact the flexible fastening member 29 and the tissue, have been blunted, rounded, and/or smoothed.

Figure 13:
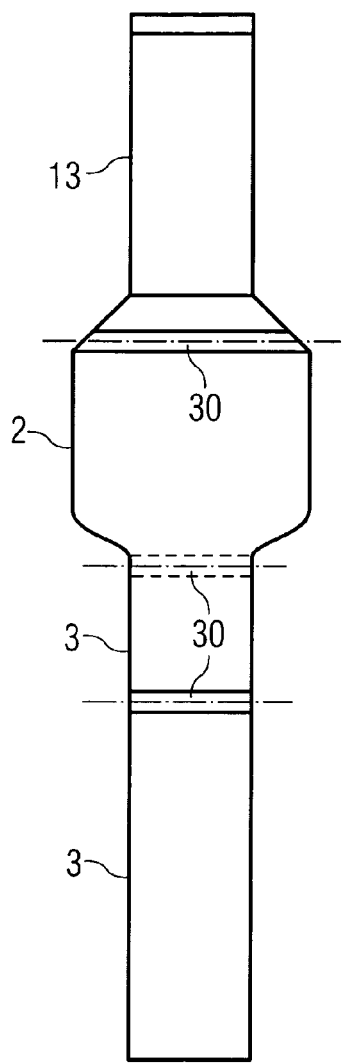
FIG. 13 shows a front view of a three-part spoon-shaped implant plate having regions of weakened material or self-interlocking hinges extending across the longitudinal axis A-A between the blade, spoon and shaft portions.

FIG. 13 illustrates a front view of a three-part, spoon-shaped implant plate 1 having at least two regions 30 of weakened material extending across the longitudinal axis A-A between the head-, shaft-, and blade portions 2, 3, 13. During surgical application of the implant plate 1, the two regions 30 of weakened material are used as strap hinges 31 or positions of separation for producing interlocking hinges 32.

Figure 14:
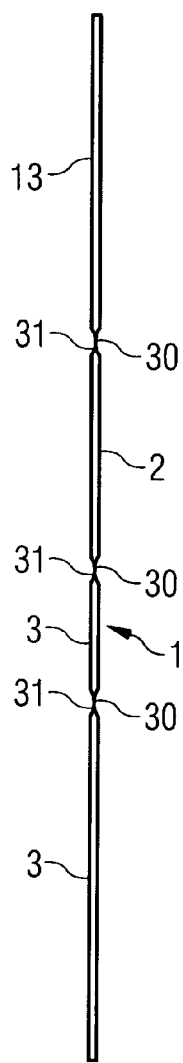
FIG. 14 shows a side view of a three-part implant plate having strap hinges between the blade and the head-end portion, and also between the head-end portion and the shaft-end portion.

FIG. 14 illustrates a side view of three regions 30 of weakened material of the implant plate 1, which can be used during later surgical application as strap hinges 31 to improve fitting to the shape of the upper-arm head and proximal upper arm, because the desired angling of the head- and blade-portions may be achieved in this manner.

Figure 15:
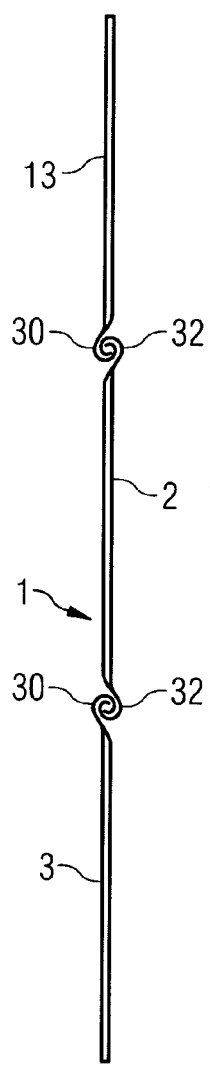
FIG. 15 shows a side view of a three-part implant plate having adjacent hinge-like interlocking portions between the blade and the head-end portion, and also between the head-end portion and the shaft-end portion.

FIG. 15 illustrates a side view of two regions 30 of weakened material of the implant plate 1, which can be used during later surgical application as self-interlocking hinges 32 to improve fitting to the shape of the upper-arm head and proximal upper arm, because the desired angling of the head- and blade-portions may be achieved also with this embodiment.

The implant plate 1 according to the invention may be designed to consist of only two parts by omitting the blade 13, wherein the region 30 of weakened material between the head-portion 2 and the shaft-portion 3 is utilized as a strap hinge 31 or a self-interlocking hinge 32 for angling and fitting to the bone 4. With the three-part embodiment of the implant plate 1, the regions 30 of weakened material may be used in combination as a strap hinge 31 and a self-interlocking hinge 32.

FIG. 16 illustrates the method as applied in a facility for manufacturing the implant plates 1. According to this, the method comprises a semi or fully automatic manufacture of implant plates 1 that are used for stabilizing a fracture of an upper-arm head and/or a fracture of a proximal upper arm. For this, a metallic strip-material 42 that is compatible with the human body, and that is available cut to length and stapled in a magazine or store 40, or as a coil 41, and that consists, for example, of implant steel, titanium, or titanium alloys, is used as a starting material for the implant plate 1. The strip material 42 is of a substantially uniform thickness of 0.5 to 6.5 mm. The strip width is governed by the respective maximum width of the head-end portion 2 of the spoon-shaped implant plate 1. The width may also be greater for the purpose of forming receiving members 6 from the strip material 42. Apart from this, the strip widths to be employed are determined by the use of the implant plates 1 for adults, young persons, or children.

In accordance with one embodiment, the strip material 42 that is available from the magazine 40 or from the uncoiling device 41 may be passed through a rolling mill 44 provided with a drilling machine 45 and/or a laser device 46 under computer control and timing. The surface of a roll of the rolling mill 44 may be profiled and may produce a nap profile, or discontinuous groove- or diamond-shaped profiles, and the like, on that side of the strip material 42 of the implant plate 1 being manufactured that will later face the bone. The drilling machine 45 and/or the laser device 46 produce the necessary drill holes 14, 23 or holes that form the apertures 7 in the receiving members 6 for the flexible fastening members 29. The strip material 42 is then processed in a punching device 47 that may be combined with the laser device 46 and/or a cutting device 48. Parallel slits 21, strip-shaped extensions 26 close to the edge, and the like, for example, are produced in these devices under program control. Subsequently the strip material 42 is processed under computer control and timing in a deep-drawing device 49 that may be combined with a bending device 50 and/or edge-rolling device 51, in order to form eyelets from parallel slits 21 or cups 24, or to form folds 22 from plate regions close to the edge, or to bend oblique cuts 28 located close to the edge at an angle, or to coil-inwards strip-shaped extensions 26 of excess material. Under computer control, the spoon-shaped final configuration is then produced, and the singling of the strip material 42 to implant plate blanks 1 is performed in a separating device 52, for which purpose use may be made of the laser device 46, the punching device 47, and/or the cutting device 48. In order to achieve an improved bearing of the implant plate 1 against the bone 4, the strip material 42 may be cold-formed to a flat channel-profile in a cold-drawing device 65 before or after the singling operation in which implant plate blanks are produced. For this, it is also possible to use the rolling mill 44 with suitable conversion, by reversing the implant plate blanks 1. Subsequently, the implant plates 1 are supplied to a deburring device 53 combined with a shot-blasting device 54, rounding device 55, and cleaning device 56. Then the implant plates 1 may be surface-finished in a coating device 57. The finishing of the implant plate 1 may be performed using galvanic, electro-chemical, or vacuum-technological coating techniques. Vacuum technological coating comprises chiefly CVD technology (chemical vapor deposition). Finally, the implant plates 1 are prepared for dispatch in a sterilizer 58 in association with packing devices 59, and sent-out for distribution.

The facility provided by the invention is of modular construction and comprises substantially the following devices, in particular, program-controlled, semi or fully automatically operated and timed manufacturing machines for performing the preparation of the metallic strip material 42, and for forming the receiving members 6 for flexible fastening members 29, and also the final configuration of the implant plates 1, possibly fitted with blades 13:

(a) at least one stacking magazine 40, and/or at least one uncoiling device 41, possibly with a deflection roller, for holding available and supplying the metallic strip material 42, (b) if required, a rolling mill 44 for at least one-sided surface profiling of the strip material 42, e.g. for producing naps, discontinuous groove-shaped or diamond-shaped profiles, and the like, on the side facing the bone 4, (c) if required, a drilling, laser-treatment, and/or punching device 45, 46, 47, in particular, a suitable automatic machine for producing apertures 7, positioned holes, or drill holes 23, and the like;

(d) if required, a laser-treatment, punching, and/or cutting device 46, 47, 48, in particular, a suitable automatic machine for preparing the strip material 42 for forming raised receiving members 6 on the side of the implant plate 1 facing away from the bone, and also, if required, a blade 13 extending from the spoon-shaped portion 2 of the implant plate blank 1;

(e) if required, deep drawing, bending, and edge-rolling devices 49, 50, 51, in particular, a suitable automatic machine for shaping the raised receiving members 6 on the side of the implant plate blank facing away from the bone 4, and also, if required, U, T, or I shaped profiles on the blade 13 by cold-forming;

(f) if required, further laser-treatment, punching, and/or cutting devices 46, 47, 48, in particular, a suitable automatic machine for producing an outer contour 8 and singling implant plate blanks 1;

(g) if required, at least one small-parts stocking device 43 for externally manufactured eyelets, hooks, or tubular sections;

(h) if required, welding, pressure welding, soldering, screwing, and/or riveting devices 60, 61, 62, 63, 64, in particular, a suitable automatic machine for attaching externally manufactured receiving members 6 for flexible fastening members 29 onto the side of the implant plate blank 1 facing away from the bone 4;

(i) if required, a cold drawing device 65, in particular, a suitable automatic machine for producing weakened material regions 30 extending across the longitudinal axis, and sharpening the free end of the blade 13, and also forming the strip material 42 to a shallow channel-shaped profile, substantially no longer extending to include the width of the blade 13;

(j) burr removing, rounding, blasting, and/or cleaning devices 53, 54, 55, 56, in particular, a suitable automatic machine for removing sharp edge regions 8, 9, 11 from the implant plates 1;

(k) if required, a coating device 57 for surface finishing, in particular, galvanic, electro-chemical, and vacuum-technological coating devices; and also (l) a sterilizer 58 and/or sterile packing device 59, in particular, a suitable automatic machine.

According to the illustrated embodiment of plant technology, the individual devices are disposed in a linear array. The devices of the plant may also be disposed in rows opposite to each other, or displaced with respect to each other in a meandering configuration. Finally, the plant may be built-up in a roundabout, turnstile, or double-star arrangement, wherein the individual devices operationally cooperate. Automatic machines having multiple functions may be applied repeatedly, making use of process and plant technology, if necessary after any needed operational conversion, so that the technical outlay of plant and devices for performing the individual method steps may be reduced by reversing the strip material 42 or the implant plate blanks 1.

According to another embodiment, the individual portions 30 of weakened material of the implant plate 1 may be utilized as strap hinges 31. The fabrication by means of process and plant technology is effected preferably in a separate cold-drawing device 65. The rolling mill 44 too may be used for cold-drawing the strip material 42 by suitable conversion, in order to produce regions 30 of weakened material in the strip material 42 under program control.

The manufacture of the two- or three-part implant plates 1 is performed in such manner that the strip material 42 is separated into the blade-, head- and/or shaft-end portions 2, 3, 13 by punching or laser-treatment. The adjacent edges of the singled portions 2, 3, 13 are formed to be self-interlocking hinges, and are connected together to be movable within limits by being fitted into each other.

In this manner an economical manufacture of the implant plates 1 is rendered possible by fabrication technology.

The implant plates 1 of the invention are used for stabilizing fractures of an upper-arm head and/or a proximal upper arm, wherein a setting of a fracture is effected by means of the implant plate 1, the head and shaft screws, and also the flexible fastening members 29 that are wound around the fractured parts, in particular the tubercle, and are used together with the receiving members 6 disposed close to the edge on the upper side of the implant plate 1. In accordance with the invention, the apertures 7 of the receiving members 6 extend substantially parallel to the outer contour 8 of the head portion 2.

Considerable surgical advantages are achieved with the invention. With the receiving members 6, it makes possible a substantially more easy and rapid threading, passing through, and also drawing-together of the flexible fastening members 29 that comprise wire cerclages or surgical suture material. With this solution, as provided by the design, substantially better setting of a fracture, and more careful treatment of bone substance is achieved. In addition, the duration of an operation is substantially shortened. Thereby a patient is relieved from physiological strain, because a use of narcotics and a loss of blood are reduced.

The invention claimed is:

1. An implant plate for stabilizing a fracture, comprising:
a plate member having an edge defining a head-end portion shaped to bear against a surface of a bone and a shaft-end portion shaped to bear against a surface of a bone, the head-end portion edge including opposite side edge sections, the shaft-end portion being narrower along a lateral direction than the head-end portion, and the plate member edge delineating a bone facing surface to bear against the bone and an opposing side surface facing away from the bone;
a plurality of holes for bone screws on each of the head-end portion and the shaft-end portion for fixing the plate member to the bone surfaces; and
discrete, integral receiving members protruding from said opposing side surface, located at the head-end portion along each side edge section, each member defining a substantially circular and circumferentially enclosed aperture through which flexible members may be passed through and tightened after the plate member has been secured to the bone surfaces, an edge circumference of each aperture having a distal curved section spaced further from said opposing side surface than a proximal curve section, wherein each discrete, integral receiving member comprises a base and a ridge provided on the base, the ridge being substantially perpendicular to the side edge section, wherein the aperture is provided within the ridge.

2. Implant plate according to claim 1, wherein a thickness of material of the implant plate including the head-end portion and the shaft-end portion is substantially uniform, wherein the head-end portion of the implant plate is widened to be of spoon-shape, and the shaft-end portion is designed to be comparatively narrower, and wherein all receiving members for the flexible fastening member are spaced along an outer edge or contour of the head-end portion.

3. Implant plate according to claim 1, wherein the receiving members are made from strip material by at least one of laser-treatment, punching, cutting, deep drawing, bending and edge-rolling, and wherein the apertures are made by at least one of drilling, punching, laser-treatment, deep drawing, or bending and edge-rolling.

4. Implant plate according to claim 1, wherein the receiving members consist of externally prefabricated ridges with drill holes, tubular receiving members, or round hooks, with or without a base, and wherein the receiving members are welded, pressure-welded, soldered, screwed, or riveted onto predetermined locating positions close to an edge of the strip material.

5. Implant plate according to claim 1, wherein the head-end portion of the implant plate has a blade disposed along an extension of a longitudinal axis, the blade having a sharp edge at one end.

6. Implant plate according to claim 5, wherein the blade has at least one drill hole having at least one screw thread into which upper-arm head-screws extending from the head-end portion of the implant plate may be screwed.

7. The implant plate according to claim 1, wherein the thickness of the plate member is 0.8 to 3.5 mm.

8. The implant plate according to claim 1, wherein the plate member is of implant steel, titanium, or a titanium alloy.

9. The implant plate according to claim 1, wherein the plate member has a slight curvature to the head-end portion and the shaft-end portion to bear against the outer surfaces of the bone.

10. The implant plate according to claim 1, wherein the plate member has a substantially uniform thickness of 0.5 to 6.5 mm.

11. The implant plate according to claim 1, wherein the opposite side edges sections are substantially parallel.

* * * * *